United States Patent [19]
Fisher et al.

[11] Patent Number: 6,056,403
[45] Date of Patent: May 2, 2000

[54] DEVICE FOR STIMULATING EYE MOVEMENT

[76] Inventors: Douglas C. Fisher, 5151 Ward Rd. #3, Wheatridge, Colo. 80033; David L. Wilson, 616 Azalea Ave., Redding, Calif. 96002

[21] Appl. No.: 09/094,394

[22] Filed: Jun. 9, 1998

[51] Int. Cl.[7] .................................................. A61B 3/10
[52] U.S. Cl. .......................................................... 351/221
[58] Field of Search .................................. 353/46, 74, 77; 340/407.1, 407.2, 815.4; 345/112, 115, 121, 123, 901; 351/200, 203, 209, 221

[56] References Cited

U.S. PATENT DOCUMENTS 4,757,302 7/1988 Hatakeyama et al. ............... 340/407.2
5,627,625 5/1997 Ogawa ........................................ 355/53

*Primary Examiner*—George Manuel
*Attorney, Agent, or Firm*—Therodore J. Bilen, Jr.

[57] ABSTRACT

A device for stimulating eye movement in a subject utilizing a hand held screen which is capable of displaying a multiplicity of visual elements. A power source illuminates the multiplicity of visual elements according to a particular selection of a visual pattern. Once selected, the visual pattern is executed and displayed by sequentially illuminating adjacent visual elements constituting groups of visual elements. The illuminated element form a cyclic pattern for scanning by the subject.

7 Claims, 5 Drawing Sheets

DEVICE FOR STIMULATING EYE MOVEMENT

BACKGROUND OF THE INVENTION

The present invention relates to a novel device for stimulating eye movement in a subject.

Stress related illnesses, such as post-traumatic stress disorder (PTSD), have been successfully treated by inducing rhythmic movement of the eye of the patient along a predetermined path, concurrently with patient imaging the traumatic event. Reference is made to U.S. Pat. No. 5,343,261 which describes a novel device for inducing eye movement in a subject in a horizontal line. In the subject patent, visual signalling elements are mounted on a surface at a certain height relative to the eyes of the patient, who is normally in a sitting position.

Although somewhat restrictive, the device found in U.S. Pat. No. 5,343,261 achieves many of its objectives. However, there is a need for a more portable and versatile device for inducing eye movement which may be used for the same purpose as the device found in U.S. Pat. No. 5,343,261.

A device for stimulating eye movement which is hand held and capable of displaying multiple visual patterns would be a notable advance in the medical field.

SUMMARY OF THE INVENTION

In accordance with the present invention a novel and useful device for stimulating eye movement in a patient is herein provided.

The device of the present invention uses a hand held screen capable of displaying a multiplicity of visual elements. The visual elements, which may be LEDs, are powered by a source and illuminated sequentially.

Means for selecting and executing a particular visual pattern of any of a plurality of patterns is achieved in the present invention. Any of the patterns chosen may be produced by sequentially illuminated selected visual elements constituting groups of visual elements on the screen. Each pattern is cyclic and is capable of inducing eye movement, which may result in saccadic eye movement, employed in the treatment of stress disorders. For example, in addition to the traditional horizontal line, back-and-forth movement, the device of the present invention may display a back-and-forth moving of a diagonal line, a closed loop pattern such as an oval, circle, figure eight, and the like. Many of the visual patterns produced by the device of the present invention include groups of visual elements that are common to other patterns. In other words, portions of the visual elements used to display a circle or oval may also be used to display portions of a figure eight pattern.

Such means for selecting and executing a particular visual pattern may include a microprocessor which is programmed to accept commands for the production of a particular pattern by the user. The selection of such patterns may be actuated by a control on the handheld screen or, remotely, using conventional remote control technology. A plurality of serial-to-parallel shift registers are also employed to drive groups or banks of LEDs. In this manner, software and hardware has been optimized for the operation of the device of the present invention.

Moreover, the device of the present invention is capable of generating a periodic audio signal commensurate with the execution of a particular visual pattern on the screen. The audio signal may possess a certain tone and speed according to the predilection of the user or administrator.

It may be apparent that a novel and useful device for stimulating eye movement has been described.

It is therefore and object of the present invention to provide a device for stimulating eye movement which is portable and may be positioned in a variety of places relative to the field of vision of the user.

Another object of the present invention is to provide a device for stimulating eye movement which is capable of producing a variety of periodic visual patterns on a screen by activating a plurality of visual elements at a certain predetermined rate.

A further object of the present invention is to provide a device for stimulating eye movement which combines visual and audio signals which are periodically or sequentially produced.

A further object of the present invention is to provide a device for stimulating eye movement which utilizes a plurality of visual elements that may be grouped into geometric forms that are common to a plurality of visual periodic patterns.

The invention possesses other objects and advantages especially as concerns particular characteristics and features thereof which will become apparent as the specification continues.

For a better understanding of the invention references made to the following detailed description of the preferred embodiment thereof which should be referenced to the prior described drawings.

DETAILED DESCRIPTION OF THE PREFERRED EMBODIMENTS

Various aspects of the present invention will evolve from the following detailed description of the preferred embodiments which should be taken in conjunction with the previously described drawings.

Figure 1:
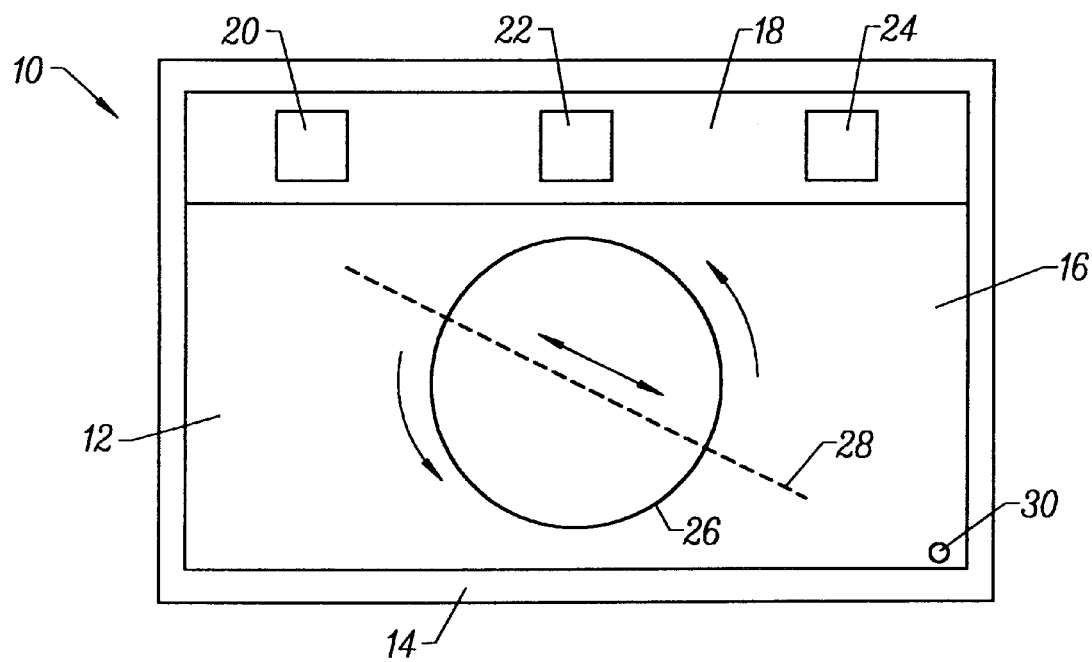
FIG. 1 is a top plan view of the handheld device of the present invention.

The invention as a whole is shown in the drawings by reference character 10. Device 10 is depicted in FIG. 1 as having a screen 12 held by a frame 14. Screen 12 includes a visual display portion 16 and a command or control portion 18. For example, a plurality of switches may be located in rectangle 20 to start and stop the electrical operation of the device, as well as to select different modes of operation. LED screen 22 would display speed settings for the cyclic or periodic patterns visually displayed or the periodic audio signals being fed to the subject using device 10. Rectangle 24 represents a power on/off switch, volume control for the audio signal, and speed up or slow down controls for the visual or audio signals.

Figure 2:
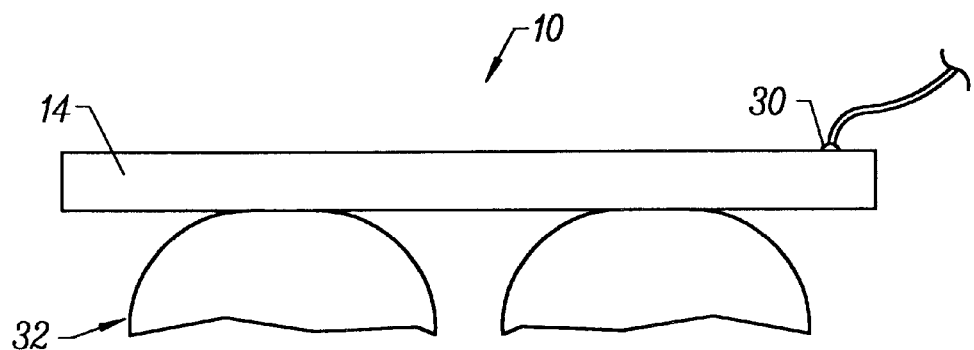
FIG. 2 is a side elevational view of the handheld device of the present invention shown resting on the knees of the user.

Screen 16 may display a variety of cyclic patterns. For example, a circle 26 as well as a diagonal line 28 are shown. It should be realized that other cyclic patterns such as a horizontal line, figure eight loop, oval, and the like may be employed in the present device. As will be detailed hereinafter, the illumination of the visual patterns, such as patterns 26 and 28 are produced by sequential illumination of visual elements. Audio jack 30 permits the user to employ head phones and the like for the audio signals produced by device 10. FIG. 2 illustrates that device 10 may be placed on the knees 32 of the user. In addition, device 10 may be held at a convenient level above the knees, on a table in front of the subject, mounted on a support at various levels relative to the eyes of the subject, and the like. In any case, device 10 is completely portable.

Figure 3:
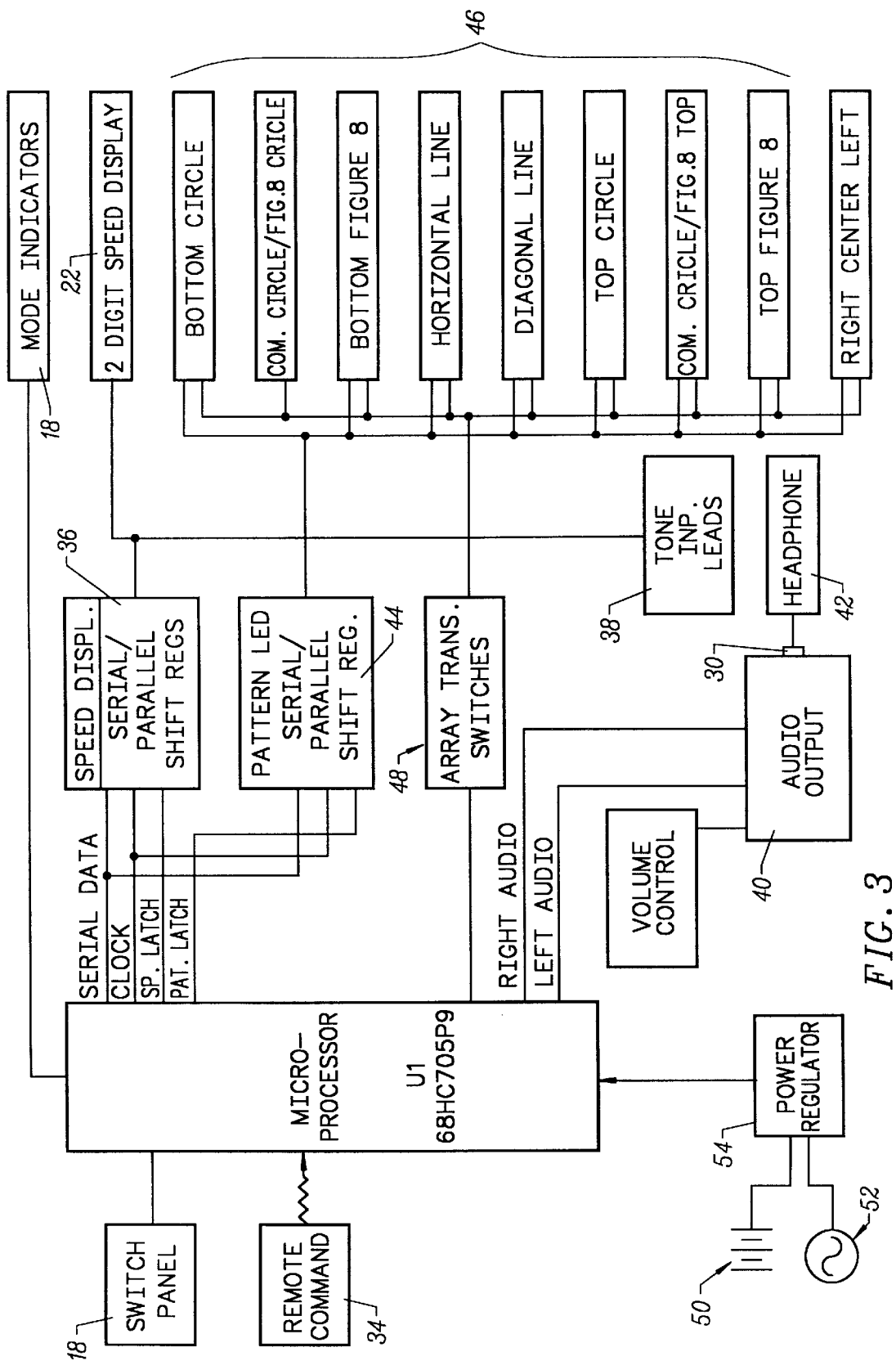
FIG. 3 is a schematic block diagram depicting the overall operation of the system of the present invention.

Turning now to FIG. 3, it may be observed that microprocessor U1 serves to control the operation of device 10 either through switch panel 18 or by a remote control element 34 producing infrared signals using conventional remote control technology. In either case, microprocessor U1 is programmed with software particular to the operation of device 10. A copy of the object code of such software is attached to this application as Appendix I. The main outputs from microprocessor U1 are the serial data, clock, speed latch, and pattern latch pins. Serial data, clock, and speed latch outputs are sent to speed display 22 found on command portion 18 of screen 12. Speed display 22 is operated through a plurality of serial/parallel switch registers 36. Tone indicator LEDs 38 are also found on speed display 22. The heretofore referenced software program provides for eight different tones from the chromatic scale. The tones are alternated through the RIGHT AUDIO and LEFT AUDIO outputs form microprocessor U1 to the audio output 40. Deck 30 on screen 12 permits the use of headphones 42 by the subject or user of device 10. It should be noted that the alternating tones produced may be independently fed to the subject or may be coordinated with the visual references, which will be hereinafter described. In any case, the alternating tones are especially useful for visually impaired subjects or subject who prefer auditory stimulation.

Visual references again originate with microprocessor U1 through the heretofore noted outputs. Pattern LED serial/shift registers 44 feed the visual signals to a plurality of LED groups 46 which are noted as being employed for the circle/oval figure eight, horizontal line, diagonal line patterns, which are cyclically produced on screen portion 16. A plurality of activators or array transistor switches 48 sequentially illuminate a plurality of LEDs found in each of the plurality of LED groups 46.

Device 10 is powered by a battery source 50 or by an AC source 52 through power regulator 54. Of course, the power requirements for the present device 10 are considered to be low voltage, in the range of 3 to 6 volts DC.

Figure 4:
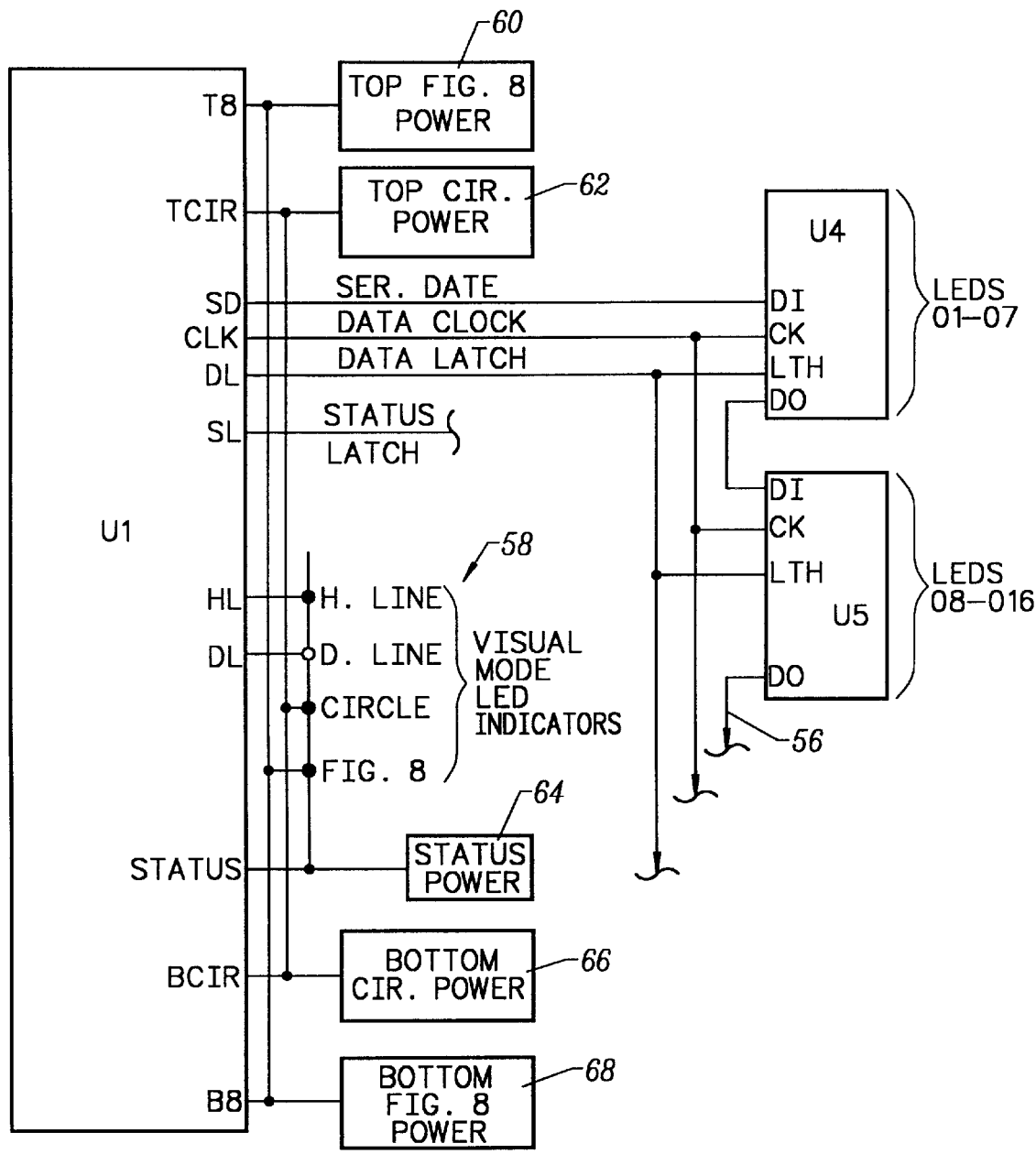
FIG. 4 is a schematic block diagram illustrating the powering and illumination of groups of LEDs.

Turning to FIG. 4, it may be observed that the power and illumination systems are depicted. Microprocessor U1 is again shown with further outputs for the various visual patterns produced on screen 12. Serial to parallel shift registers U4 are typical of a multiplicity of such devices. For example, U4 controls LEDs 1 through 7 on screen 12, U5 controls LED 08 through 016 on screen 12 and so forth through other serial to parallel shift registers following output arrow 56 from U5. Plurality of visual mode indicators 58 are also shown and appear on screen 12 to the user. In addition, power supply blocks 60–68 indicate the power sent to particular groups of LEDs forming portions of the visual pattern 16 on screen 12.

Figure 5:
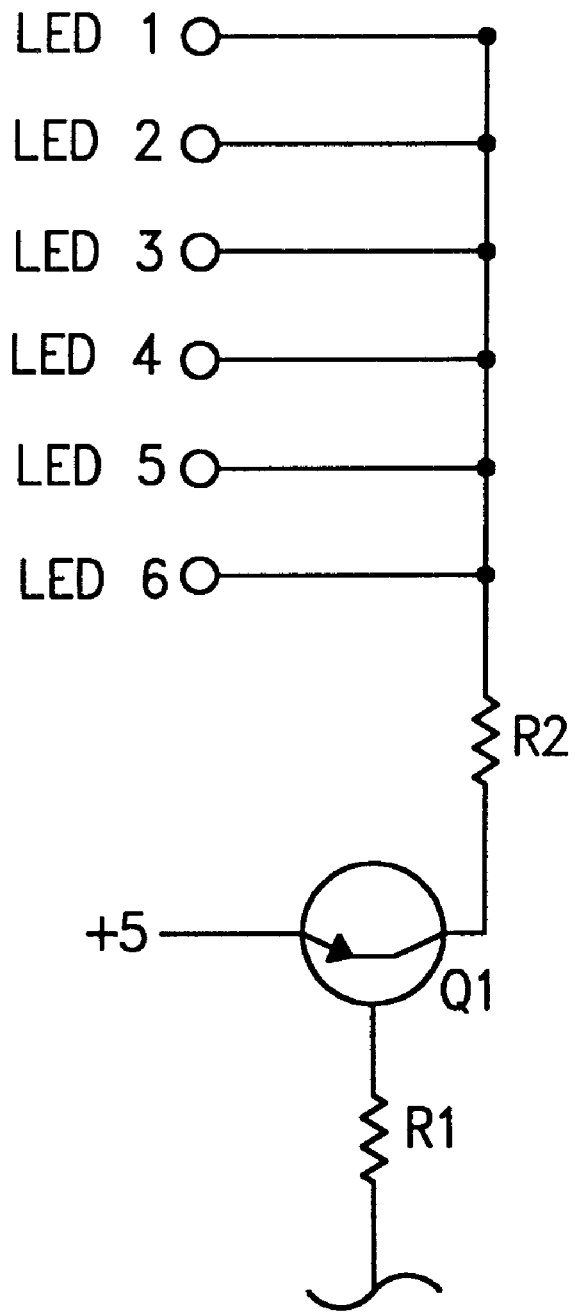
FIG. 5 is a schematic view of a typical switching arrangement for a group of LEDs.

Turning to FIG. 5, it may be seen that a typical array transistor switch Q1 of plurality of such switches 48, is depicted with respect to the common group of LEDs 1–6, which form the common portion of a circle or oval as well as a portion of a figure eight pattern. In this regard, voltages passed to transistor switch Q1 passes through resistor R2 to LEDs 1–6, which are sequentially illuminated. The same switching arrangement exists for other groups of LEDs which will become apparent as the specification continues.

Figure 6:
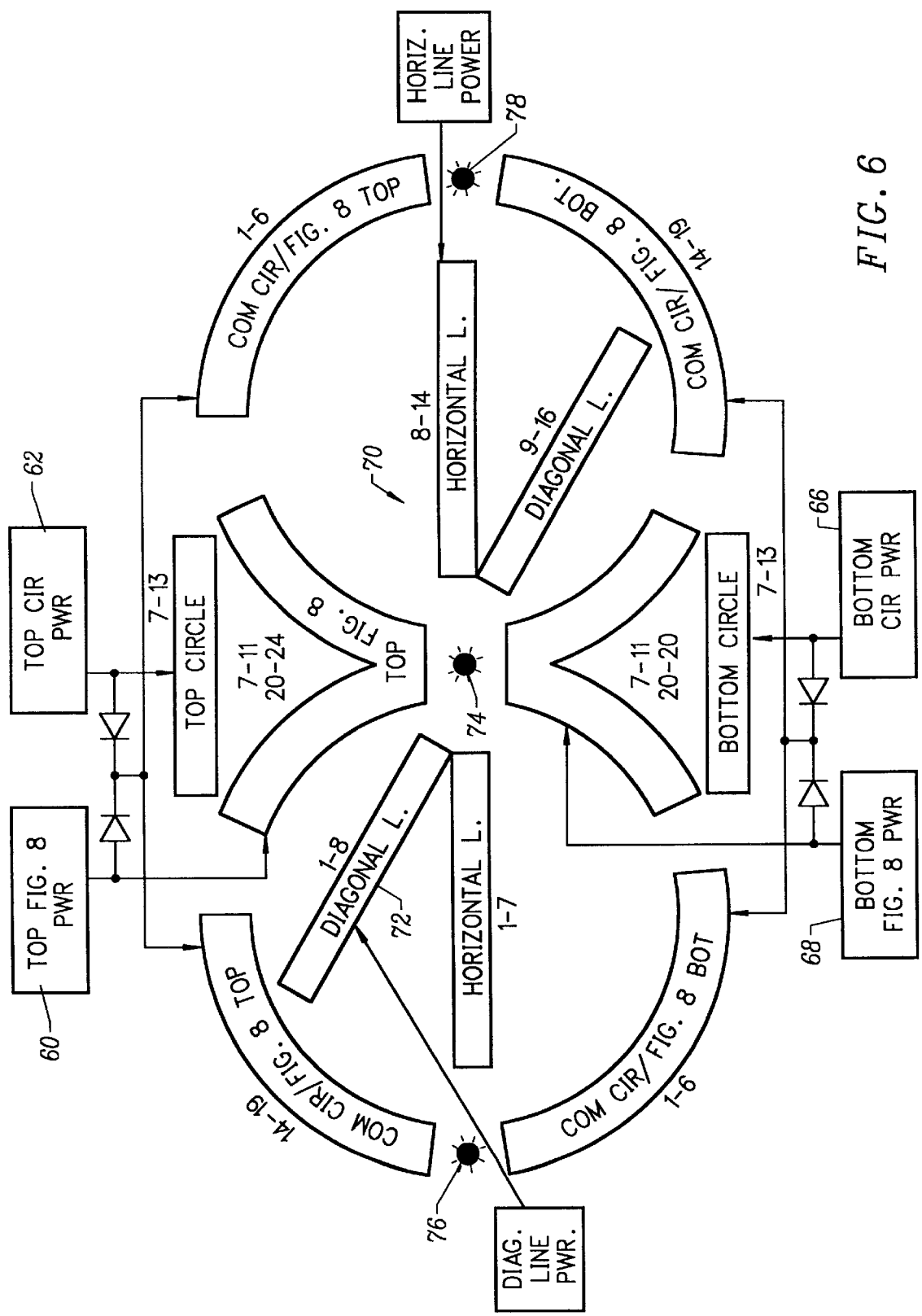
FIG. 6 is a schematic diagram of the activation of common groups of LEDs constituting patterns visually produced by the device of the present invention.

FIG. 6 illustrates typical groups of LEDs which are used to produce the various pattern 16 on screen 12. Power is provided to the various groups of LEDs by the power outputs shown on FIG. 4 and which are labeled by blocks 60–66. Although, horizontal and diagonal line groups of LEDs 70 and 72 only share a common LED 74, the circle and figure eight patterns share the left, right, top, and bottom circular groups utilizing diodes 1–6 and 14–19 as noted. In addition, common LEDs 76 and 78 are found at the conflux between the top and bottom of the circle and figure eight patterns.

In operation, the system is initialized by preprogrammed microprocessor U1. Microprocessor U1 checks switch panel 18 and the infrared input from control unit 34. Possible commands are START, STOP, SPEED UP, SLOW DOWN, CHANGE VISUAL SCANNING MODE, or CHANGE AUDIO TONE. For the circuitry depicted in the drawings, scanning begins from the center resting position at LED 74 while the speed, tone, and mode indicators are turned off. The start-up scan mode for a visual pattern, derives from the horizontal line groups of LEDs 70. Scanning continues until the STOP mode command is received. When a new scan mode is received, the next mode is not started until the center position at LED 74 is encountered. When center LED 74 is reached, scanning stops and the speed, mode, and tone indicator LEDs are illuminated on screen portion 18 of screen 12.

When the SPEED UP command is received by initiation of a control signal at rectangle 24 found on command portion 18 of screen 12, the delay-between-LEDs variable is reduced so the scan speed is increased. The speed display found at monitor 22 of screen 12 is updated to reflect the new speed value. For example, the fastest speed of scanning for device 10 may be displayed as the numeral 40, while the slow speed may be displayed as one. Of course, other values may be used in the same regard. When a SLOW DOWN command is received, the delay-between-LEDs variable is increased so the scan speed is decreased. LED display is updated to reflect the new speed value in a similar manner to the process described for "speed up", above.

As heretofore noted, there are four different scanning patterns which may be displayed on screen portion 16: horizontal line, diagonal line, circular pattern (oval), and sideways figure eight or infinity pattern. The four patterns are selected in sequence each time the scanning mode command is received by the controls found in area 20 on screen 12. Visual scan mode indicators are updated when the change scan mode command is received. However, these indicators are not displayed when scanning.

The audio tones generated by device 10 of the present invention consist of eight notes from the scale ranging from C, (approximately 131 hz) up to C, an octave higher. The tone frequencies are generated in the microprocessor U1 using an internal counter/timer which is programmed by the software of Appendix I to give the proper frequencies for each note. Each time a command is received to change the audio tone, either by switch panel 18 or remote command module 34, the microprocessor U1 loads the next tone value into the counter/timer, therewithin. The tone indicator LEDs are updated on command portion 18 of screen 12 to display the correct note when scanning is stopped. It should be realized that the present system optimizes the software and hardware needed to produce the variety of visual patterns and audio tones used in the present invention. It should be noted that the LED banks or groups displayed on FIG. 6 may also employ the same or similar code in the software found in Appendix I. For example, by grouping the top half of the circle and the bottom half of the circle in similar banks, the software code can simply sequence through the top half of the circle, switch off the top half of the circle, switch on the bottom half of the circle, and repeat the same code.

While in the foregoing, embodiments of the present invention have been set forth in considerable detail for the purposes of making a complete disclosure of the invention, it may be apparent to those of skill in the art that numerous changes may be made in such details without departing from the spirit and principles of the invention.

What is claimed is:

1. A device for stimulating eye movement in a subject, comprising:
   a. a hand-held screen capable of displaying a multiplicity of visual elements;
   b. a power source for illuminating said multiplicity of visual elements; and
   c. means for selecting and executing a particular cyclic visual pattern of a plurality of cyclic visual patterns, produced by sequentially illuminating selected visual elements of groups of said visual elements on said screen in a cyclic pattern for scanning by the subject, said means for executing a particular cyclic visual pattern of a plurality of cyclic visual patterns comprising a plurality of activators for sequentially illuminating said selected visual elements of groups of said visual elements.

2. The device of claim 1 in which said means for selecting and executing a particular visual pattern includes a microprocessor and a plurality of serial-to-parallel shift registers to sequentially power a selected group of visual elements.

3. The device of claim 2 in which a selective one of said shift registers is configured to power a group of visual elements common to at lest two of said multiplicity of cyclic patterns.

4. The device of claim 1 which additionally comprises means for generating a periodic audio signal to the subject during execution of a particular visual cyclic pattern.

5. The device of claim 4 in which said means for selecting and executing a particular visual cyclic pattern includes a microprocessor and a plurality of serial-to-parallel shift registers to sequentially power a selected group of visual elements.

6. The device of claim 5 in which a selective one of said shift registers is configured to power a group of visual elements common to at lest two of said multiplicity of cyclic patterns.

7. The device of claim 4 which additionally comprises a headset for hearing said periodic audio signal.

\* \* \* \* \*